United States Patent [19]

Greff et al.

[11] 4,370,315

[45] Jan. 25, 1983

[54] POST-DEPILATORY COMPOSITION REDUCING PROGRESSIVELY THE GROWTH OF BODY HAIR

[75] Inventors: Daniel Greff, Plaisir; Françoise Petit-Martenon, Paris; Tran Toan, La Verriere, all of France

[73] Assignee: Sederma, Meudon, France

[21] Appl. No.: 879,929

[22] Filed: Feb. 22, 1978

[30] Foreign Application Priority Data

Feb. 22, 1977 [FR] France .................. 77 05158

[51] Int. Cl.³ .............................................. A61K 37/48
[52] U.S. Cl. ...................................... 424/94; 424/73; 424/314; 424/366
[58] Field of Search ........................................... 424/94

[56] References Cited

FOREIGN PATENT DOCUMENTS

644M 7/1961 France .................. 424/94

Primary Examiner—Dale R. Ore
Attorney, Agent, or Firm—Sughrue, Mion, Zinn, Macpeak & Seas

[57] ABSTRACT

The process consists in incorporating into the preparations enzymes called lipoxygenases together with their substrate named linoleic acid.

The excipients of these preparations are chosen in a way as to ensure preservation of the active agents, easy spreading and rapid cutaneous absorption.

The preparations from the invention are used to progressively reduce the growth of body hair after depilation. This reduction is perceptible after several depilatory operations followed by the application of these preparations.

6 Claims, No Drawings

POST-DEPILATORY COMPOSITION REDUCING PROGRESSIVELY THE GROWTH OF BODY HAIR

This invention concerns a new way of extending the duration of depilation carried out with classical methods, such as complete extraction of body hair on humans and living animals with the help of depilatory nipper, wax or paste. In this case, it takes about 2 or 3 weeks before new hair appears. This makes frequent renewal of the depilation procedure necessary. Furthermore, these operations are very irritating for the skin, and other soothing and softening preparations are needed.

The said invention concerns a new process of extending the action of depilation by reducing noticeably the fresh growth of hair.

From Kantorowicz's observations made in 1907 (German Pat. No. 196 617), it was shown that some metallic peroxides and peroxidized anions delayed the growth of body hair. In the same objective, the authors of the present invention have noticed more precise facts, and proposed new means without the disadvantages of the peroxidized compounds cited hereabove.

The invented process consists in incorporating enzymes with their substrate into the preparation. These enzymes are lipoxygenases, extracted from soya beans (G. Hispida), classified: EC 1.13.11.12 [1]. They are commercially available under the name of lipoxydase. Lipoxygenases of different vegetal origin could be used as well.

The substrate used is linoleic acid, also called vitamin F acid. Its derivatives, such as methyl-, ethyl-, glyceric esters, diethanolamide or its metallic soaps (sodium or potassium) can also be used as substrate, in the same way as $\alpha$ linolenic or $\gamma$ linolenic acids. One remarks that linoleic acid is normally present in fatty acids of the human skin, at about 0.65% for a healthy skin [2].

The preparations which incorporate these substances are ointments, creams, milks, lotions and generally any cosmetics preparation either fluid or not. The dosage is 250,000 to 1,000,000 enzymatic activity units [3] for 100 grams of end-product. The substrate represents 0.5 to 2% w/w. The preparation may also contain classical substances which are interesting for the above-mentioned use.

For example, the following formula can be used for a lotion:

| | |
|---|---|
| Tegin [4] | 2.500 |
| Cetiol HE [5] | 0.200 |
| P.E.G. 400 | 3.500 |
| Water | 90.290 |
| Titanium dioxyde | 1.000 |
| Propylene glycol | 0.800 |
| Preservative | 0.300 |
| Linoleic acid | 1.000 |
| Lipoxidase | 0.010 |
| Menthol | 0.100 |
| Fragrance | 0.300 |
| Polysorbate 20 | 0.500 |
| Sodium borate | q.s.p. pH 8.0 |

The lipoxygenases used had an activity of 48,000 A.U./mg. One can of course use batches with other specific activities by changing proportionally the amount of enzymes.

This lotion was used by 20 female volunteers, aged 20 to 35, after depilation of certain body parts (legs, arms, under-arms). The lotion is uniformly and quickly spread over the depilated parts, using 1 g. per 50 sq. cm, by slight massages. The absorption is fast and leaves no greasy film; the depilation can then be renewed either on an adjoining region or on the same spot, if the first operation was insufficient.

No subject experienced irritation, not even on normally sensitive parts (under-arms, internal surface of legs). A feeling of freshness was noted every time.

On 16 cases, i.e. 80%, fresh growth of hair was clearly perceptible only 6 or more weeks later. Volunteers using this preparation for several and successive depilations at the same parts noted that hair growth was delayed progressively up to 2 months. Moreover, they noticed a decreasing density of hair.

All these volunteers had used classical commercial preparations in the past. Under these conditions, the regrowth of hair was complete after 3 weeks at the latest.

The products obtained by reaction of lipoxygenases on the above-mentioned substrates are their hydroperoxides. When the substrate is linoleic acid, the principal product is 13-L-hydroperoxy-cis, trans-9, 11-octadecadienoic acid [6], under the physical conditions of manufacture and use of these preparations: moderately alkaline medium ($8 \leq pH \leq 9$), ambient temperature and exposure to the air.

Another achievement of this invention is the fact that the hydroperoxides of linoleic or linolenic acids, previously synthesized by chemical or biological ways, then purified, can be incorporated directly into cosmetic preparations.

It has been shown that the peroxides of linoleic acid considerably change the ionic conductivity of phospholipidic membranes in alkaline medium [7]. We suggest that the observed effect is related to this increased membrane conductivity, particularly to the bottom of the follicle where the metabolism leading to the growth of the hair takes place.

REFERENCES

[1] Enzyme Nomenclature, Recommendations (1972) of the IUPAC-IUB, p. 104, American Elsevier Pub. Co., New York, NY, (1973).

[2] Krakow R., Downing D. T., Strauss J. S., and Pochi P. E., J. Invest. Dermatol., 61, 286 (1973).

[3] Enzyme Nomenclature, Recommendations (1972) of the IUPAC-IUB, p. 26, ibid.

[4] Trade mark of Theodor Goldschmidt AG, Essen, W. Germany.

[5] Trade mark of Henkel GmbH, Düsseldorf, W. Germany.

[6] Leu K., Lebensm.-Wiss. Technol., 7, 82 (1974).

[7] Antonov V. F., Vladimirov Yu. A., Rossel's A. N., Korkina L. G., Korepanova Ye. A. and Trukhmanova K. I., Biofizika, 18, 668 (1973).

We claim:

1. A process to treat man or other living animals to slow down new growth of body hair after depilation which comprises applying to parts of man or living animals where removal of body hair is desired in an amount and at a frequency sufficient to retard new hair growth a cosmetic preparation consisting essentially of a cosmetic cream, ointment, milk or lotion having incorporated therein at least one lipoxygenase in an amount such that the total lipoxygenase enzyme activity is from 250,000 to 1,000,000 units per 100 grams of said cosmetic preparation and linoleic acid or derivative thereof in amount of 0.5 to 3% of mass of said cosmetic preparation.

2. The process of claim 1 wherein the linoleic acid is in the preparation at 0.5 to 2% of the mass of the final product.

3. The process of claim 1 wherein the preparation contains a linoleic acid derivative selected from the group consisting of the ester, amide and metal-soap derivatives thereof in the preparation at 0.5 to 3% of the mass of the final product.

4. The process of claim 1 wherein the preparation contains $\alpha$-linolenic acid, $\gamma$-linolenic acid, or a mixture thereof in the preparation at 0.5 to 2% of the mass of the finished product.

5. The process of claim 1 wherein at least one hydroperoxide of linoleic acid is incorporated into the preparation at 0.5 to 2% of the mass of the finished product.

6. The process of claim 1 wherein at least one hydroperoxide of $\alpha$ or $\gamma$ linolenic acid is incorporated into the preparation at 0.5 to 2% of the mass of the final product.

* * * * *